United States Patent [19]
Fujiwara et al.

[11] Patent Number: 6,090,730
[45] Date of Patent: *Jul. 18, 2000

[54] FILAMENT NON-WOVEN FABRIC AND AN ABSORBENT ARTICLE USING THE SAME

[75] Inventors: Toshikatsu Fujiwara; Taiju Terakawa; Shigeyuki Sugawara, all of Shiga, Japan

[73] Assignee: Chisso Corporation, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/983,401

[22] PCT Filed: Jun. 23, 1997

[86] PCT No.: PCT/JP97/02165

§ 371 Date: Jan. 20, 1998

§ 102(e) Date: Jan. 20, 1998

[87] PCT Pub. No.: WO97/49853

PCT Pub. Date: Dec. 31, 1997

[30] Foreign Application Priority Data

Jun. 26, 1996 [JP] Japan .................................. 8-166422

[51] Int. Cl.$^7$ .................................................... D04H 3/14
[52] U.S. Cl. .................... 442/361; 442/362; 442/364; 442/365; 442/401; 442/417
[58] Field of Search ................................ 442/361, 362, 442/364, 365, 401, 417

[56] References Cited

U.S. PATENT DOCUMENTS

| | | | |
|---|---|---|---|
| 5,064,599 | 11/1991 | Ando et al. ............................ | 264/237 |
| 5,126,201 | 6/1992 | Shiba et al. ............................ | 428/389 |
| 5,498,468 | 3/1996 | Blaney .................................... | 428/198 |
| 5,605,749 | 2/1997 | Pike et al. ............................... | 442/60 |
| 5,652,051 | 7/1997 | Shawver et al. ....................... | 442/362 |

FOREIGN PATENT DOCUMENTS

| | | |
|---|---|---|
| 0 579 883 | 1/1994 | European Pat. Off. . |
| 59-173312 | 10/1984 | Japan . |
| 2-169718 | 6/1990 | Japan . |
| 3-279417 | 12/1991 | Japan . |
| 3-287875 | 12/1991 | Japan . |
| 4-136252 | 5/1992 | Japan . |
| 5-5261 | 1/1993 | Japan . |
| 5-263350 | 10/1993 | Japan . |

OTHER PUBLICATIONS

1997 International Search Report for PCT/JP97/02165.

*Primary Examiner*—Helen L. Pezzuto
*Attorney, Agent, or Firm*—Merchant & Gould P.C.

[57] ABSTRACT

A filament non-woven fabric comprising thermoplastic conjugated filaments comprising at least one low melting point resin or low softening point resin selected from the group consisting of olefin binary copolymer or olefin terpolymer as the first component and crystalline thermoplastic resin as the second component. The thermoplastic conjugated filament contains inorganic powder in at least the first component, wherein the content of the inorganic powder is 500 to 50000 weight ppm with respect to the fibers. The present invention can provide a filament non-woven fabric that is excellent in the high adhesive property, low temperature adhesive property, hand feeling such as softness or touch etc., and uniformity. Furthermore, operating efficiency such as the spinning property is good. Absorbent articles can be produced using the above mentioned filament non-woven fabrics.

11 Claims, 3 Drawing Sheets

FILAMENT NON-WOVEN FABRIC AND AN ABSORBENT ARTICLE USING THE SAME

TECHNICAL FIELD

The invention relates to a filament non-woven fabric. In particular, the invention relates to a non-woven fabric comprising thermoplastic conjugated filaments comprising at least one low melting point or low softening point resin selected from olefin binary copolymer or olefin terpolymer as a first component and a crystalline thermoplastic resin as a second component and an absorbent article using the above mentioned filament non-woven fabric.

BACKGROUND TECHNOLOGY

A spun bond non-woven fabric as a typical example of a filament non-woven fabric is produced by a method wherein a group of filaments discharged from a spinneret for melt spinning are drawn and stretched by introducing into an air sucker etc., opened, and accumulated on a collecting conveyor to be formed into a filament web; and then the filaments are entangled or thermally adhered by appropriate means. Therefore, since this non-woven fabric comprises filaments, namely, continuous fibers, it is more excellent in the mechanical properties such as tensile strength etc. as compared with a staple fiber non-woven fabric comprising short fibers. Moreover, since this non-woven fabric is produced by opening and accumulating the filaments obtained directly by melt spinning, it can be rationally produced as compared with non-woven fabrics obtained by opening and accumulating staple fibers by a dry method or a wet method. In recent years, the production of such non-woven fabrics has radically increased.

In particular, a non-woven fabric that comprises conjugated filaments comprising a low melting point resin or a low softening point resin comprising olefin binary copolymer or terpolymer as one component and a crystalline thermoplastic resin as another component is not only advantageous as a filament non-woven fabric from the above mentioned viewpoint, but also is excellent in thermal adhesion, and thus it is easily processable. In a case where the non-woven fabric having excellent properties can be produced, the demand for such non-woven fabric is expected to radically increase.

Moreover, conventionally, absorbent articles such as disposable diapers like paper diapers, sanitary napkins and the like have structures so that body fluids such as urine, blood or the like are absorbed and leakage is prevented. Although the specific structure of such absorbent articles varies between respective embodiments, however, such an absorbent article comprises at least an absorptive core layer for absorbing and retaining body fluids such as urine, blood or the like; a liquid permeable top sheet produced from, for example, a non-woven fabric and located at the side of the front surface of the core layer (the side contacting with the user's skin); and a liquid impermeable back sheet located at the back side of the core layer that prevents the absorbed body fluids from leaking outside. Moreover, in general, in absorbent articles such as disposable diapers like paper diapers or sanitary napkins and the like, in addition to the back sheet, water repellent side sheets are provided at both sides of the absorbent articles so as to prevent absorbed liquid such as body fluids from leaking when the absorbent articles are displaced from the desired place due to the user's physical motion or when a user lays down on his/her side. (In the case of disposable diapers, since the water repellent side sheets often are provided with gathers, they are called a side gather or a leg cuff etc. In the case of disposable diapers, such side sheets are provided in a place that holds the joints of the thigh or the circumference of the thigh.) In addition, in the disposable diapers, a water-repellent round sheet comprising a non-woven fabric or the like also is provided at the skin side of the portion covering the abdomen or the portion covering the upper buttock located opposite to the abdomen, in order to prevent the liquids such as body fluids or the like, which are absorbed by the absorbent articles and which leak to the abdomen portion or the upper buttock portion, from leaking outside of the absorbent articles when the user falls down or lays down or turns the body. Moreover, in the disposable diapers, a belt-like waist gather etc. often is provided in the waist portion. Such gathers also comprise a water repellent sheet comprising a non-woven fabric or the like.

Moreover, for the core layer, various kinds of appropriate absorptive core layers are used. Such absorptive core layers comprise the compressed mixture in which an aggregate of fibers comprising cellulose type fiber such as fluff pulp etc., with which if necessary further synthetic fibers mixed, and a high water absorptive resin are mixed and compressed to harden. This absorptive core layer is, in general, wrapped up by, for example, tissue paper. Moreover, as a back sheet, a thermoplastic film is usually used. The thermoplastic film has a large number of minute micropores so as to prevent stuffiness inside when worn and to provide ventilation. Moreover, from the view point of improving the plastic-like touch and appearance peculiar to films, or from the viewpoint of improving the strength, the composite comprising a film and a non-woven fabric also is used. In addition, in order to provide various kinds of functions, there are absorbent articles comprising additional layers to which the other sheets are inserted further. Necessary portions between these sheets are adhered by using appropriate hot melt type adhesives or by means of thermal compression bonding.

However, the hot melt type adhesives have stickiness, so that the adhesive strength is no more strong than the case of adhesion with the pressure sensitive adhesives is. Furthermore, if too much hot melt type adhesives is used, clogging in each sheet occurs, thus damaging the ventilation or deteriorating permeability with respect to body fluid. Moreover, in a case where the conventional filament non-woven fabric comprising a single component is used for each member of these absorbent articles and bonded by thermal compression bonding, the adhesive strength is insufficient or the bonded portion tends to be ruptured because of the damage by thermal compression.

Olefin binary copolymer or olefin terpolymer such as ethylene-propylene random copolymer or ethylene-butene-propylene random copolymer used as a thermal adhesive component of the non-woven fabric comprising thermal adhesive conjugated filaments shows a relatively low tacticity, a low crystallization property, low melting point or low softening point properties by introducing ethylene or ethylene and butene into the polypropylene molecular chain. Moreover, the frictional resistance between fibers or between fiber and metal is relatively high, although they differ depending on the additive ratio of ethylene or ethylene and butene.

Therefore, there are some problems: when fibers discharged from the spinning nozzle holes are drawn by the metallic air sucker, the non-uniformity of fineness occurs due to the friction between metals or between fibers; or the fibers form bundles and are not easily opened.

Moreover, in a case where the resin having low crystallinity is used like the above, the time or distance (solidification length) in which resin fiber discharged from the spinning nozzle holes in a melting state is crystallized and solidified becomes remarkably long.

Therefore, in such non-woven fabrics, filaments form bundles due to the friction and non-uniformity of fineness or poor opening occurs, and furthermore the distance between filaments is short. As a result, filaments whose solidification length becomes long contact with each other in a molten state, namely, in a state where a low melting point or a low softening point olefin copolymer is melting, thus causing so called filament breakage and deteriorating the operating efficiency.

JP-A 5-5261 discloses the non-woven fabric made of conjugated filaments comprising ethylene-propylene random copolymer and isotactic polypropylene. In this disclosure, however, no way to avoid the above mentioned problems is particularly described.

Moreover, JP-A 5-263350 discloses a filament non-woven fabric in which the softness is enhanced by using ethylene-propylene random copolymer alone, and the above mentioned non-uniformity of fineness, poor opening, and the operating inefficiency due to the filament breakage are improved by adding nucleating agents. Therefore, it is thought that if the above mentioned two techniques are combined, even a conjugated filament in which one part of olefin binary copolymer or terpolymer such as ethylene-propylene random copolymer or ethylene-butene-propylene random copolymer is exposed to the surface of the filament can easily provide a non-woven fabric which is excellent in the uniformity.

However, in the technique disclosed in JP-A 5-263350, 3-methyl-1-butene copolymer that is a resin exhibiting a strong nucleating effect is used as the nucleating agent of ethylene-propylene random copolymer.

Consequently, the use of this nucleating agent results not only in an increase in crystallization initiation temperature but also enhances the orientation crystallization of ethylene-propylene random copolymer having an increased tension in melting state at the time of high speed spinning that is peculiar to the spun bond method. The resultant filaments have a much higher melting point or softening point than that of ethylene-propylene random copolymer resin itself. Moreover, the filaments having the fine fineness cannot be obtained easily due to the increase of the melt tension. Furthermore, in a case where the filaments having fine fineness are spun in this state, a tension greater than the breaking strength of melting filaments is developed, thus causing filament breakage.

In other words, in the technique disclosed in the above mentioned Laid Open Patent, the characteristics such as softness, excellent adhesiveness or low temperature adhesive property or the like of the low melting point or low softening point olefin copolymer such as ethylene-propylene random copolymer or ethylene-butene-propylene random copolymer cannot be fully brought out, and therefore the resultant filament non-woven fabrics are not sufficient in the hand feeling such as softness or touch etc.

The object of the present invention is to avoid the above mentioned problems and to provide a filament non-woven fabric comprising conjugated filaments having a high adhesive property, an excellent low temperature adhesive property, providing the resultant filament non-woven fabric with an excellent hand feeling such as softness or touch etc, and uniformity of the non-woven fabric, and having a high operating efficiency such as spinning property.

Another object of the present invention is to avoid the above mentioned problems of the conventional absorbent articles and by using the above mentioned filament non-woven fabric in at least one portion of the absorbent article to provide an absorbent article which has an excellent hand feeling such as softness or touch etc. and which is well adhered to the other members so that layers constituting the absorbent articles are not peeled apart or do not lose their shape at the time of using.

The present inventors intensively investigated and found that if inorganic powder is added at least to the first component, namely, a low melting point component or low softening point component, and the inorganic powder is exposed to the surface of fibers, minute unevenness is provided on the surface of fibers and the area where the fibers contact with each other is reduced, and adhesion between the fibers during spinning can be inhibited, so that filament breakage is decreased to make the operating efficiency good. It also was found that when inorganic powder is added, the crystallization temperature of olefin copolymer hardly increases and the increase in the crystallization is remarkably small, and therefore a filament non-woven fabric which is excellent in hand feeling such as softness or touch etc. can be obtained without damaging the properties of low melting point or low softening point olefin copolymer, for example, softness, excellent adhesion properties, low temperature adhesion properties or the like. It also was found that when such filament non-woven fabric is used for at least one portion of the absorbent article, the absorbent article is excellent in hand feeling such as softness or touch etc., with good adhesion between the other members so that the layers of absorbent articles are not peeled apart from other layer are not broken, thereby reaching the present invention.

DISCLOSURE OF INVENTION

The filament non-woven fabric of the present invention is a filament non-woven fabric comprising thermoplastic conjugated filaments comprising at least one low melting point resin or low softening point resin that is selected from the group consisting of olefin binary copolymer and olefin terpolymer as a first component and crystalline thermoplastic resin as a second component; and the thermoplastic filament contains inorganic powder in at least the first component, wherein the content of the inorganic powder is 500 to 50000 weight ppm in the concentration with respect to filament.

It is preferable in the filament non-woven fabric of the present invention that the olefin terpolymer is ethylene-butene-propylene copolymer comprising 84 to 97 wt. % of propylene, 1 to 15 wt. % of 1-butene and 1 to 10 wt. % of ethylene.

It is preferable in the filament non-woven fabric of the present invention that the olefin binary copolymer is ethylene-propylene copolymer comprising 85 to 99 wt. % of propylene and 1 to 15 wt. % of ethylene.

It is preferable in the filament non-woven fabric of the present invention that the olefin binary copolymer is butene-propylene copolymer comprising 50 to 99 wt. % of propylene and 1 to 50 wt. % of 1-butene.

It is preferable in the filament non-woven fabric of the present invention that the olefin binary copolymer is ethylene-octene copolymer comprising 73 to 99 wt. % of ethylene and 1 to 27 wt. % of 1-octene.

It is preferable in the filament non-woven fabric of the present invention that the particle diameter of the inorganic powder is in the range of 0.04 to 2 $\mu$m.

It is preferable in the filament non-woven fabric of the present invention that the inorganic powder is at least one inorganic powder selected from the group consisting of titanium dioxide, silica, alum, calcium carbonate, calcium oxide, magnesium oxide and talc.

It is preferable in the filament non-woven fabric of the present invention that the crystalline thermoplastic resin as the second component is polypropylene.

It is preferable in the filament non-woven fabric of the present invention that the crystalline thermoplastic resin as the second component is polyethylene terephthalate.

It is preferable in the filament non-woven fabric of the present invention that the filament non-woven fabric according is obtained by the spun bond method.

Moreover, the absorbent article of the present invention is the absorbent article using the filament non-woven fabric described in any of the above items in at least one part of the absorbent article.

BEST MODE FOR CARRYING OUT THE INVENTION

Figure 1:
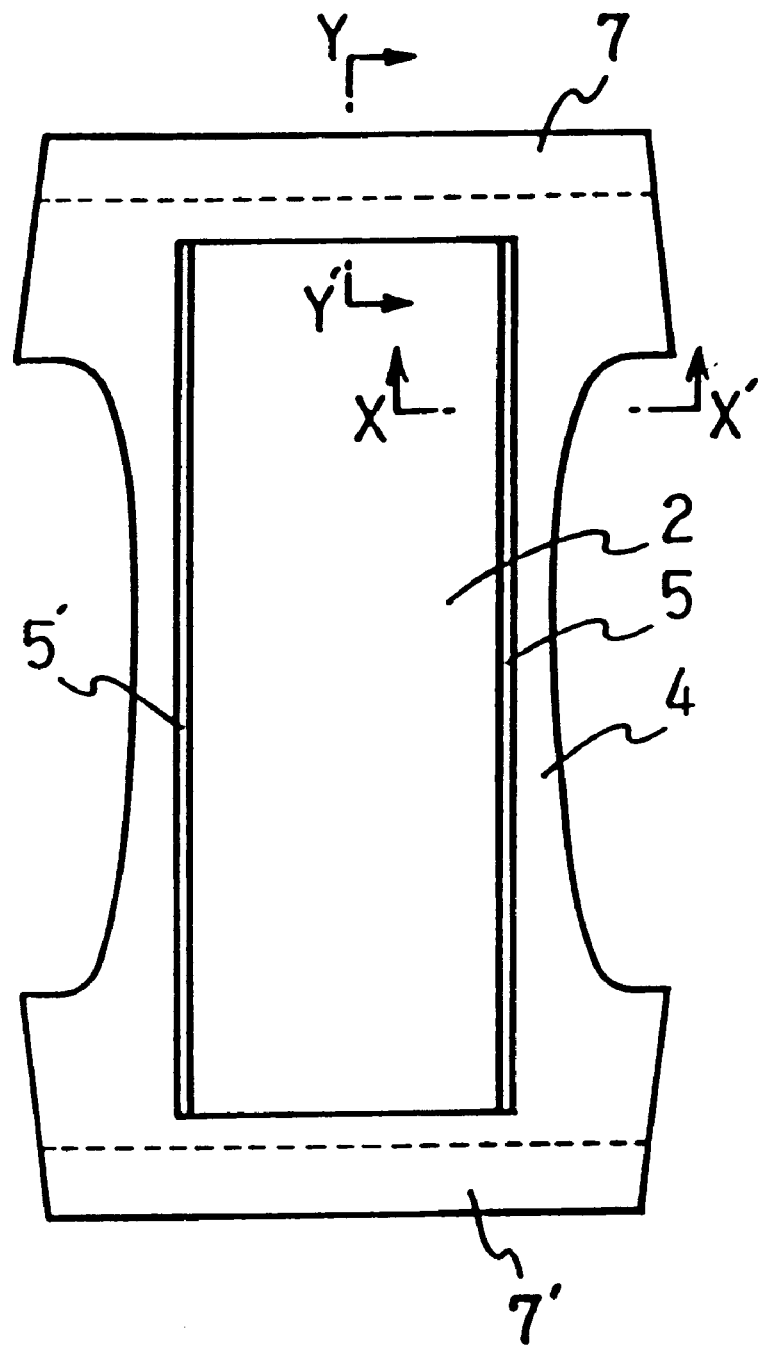
FIG. 1 is a plan view of one embodiment of a disposable diaper using the filament non-woven fabric of the present invention in one part of a disposable diaper when viewed from the side of the user's skin.

The filament non-woven fabric of the present invention is a filament non-woven fabric comprising thermoplastic conjugated filaments comprising at least one low melting point resin or low softening point resin (hereinafter, low melting point resin will be used for abbreviation) that is selected from the group consisting of olefin binary copolymer and olefin terpolymer as a first component and crystalline thermoplastic resin as a second component; and the thermoplastic filament contains inorganic powder in at least the first component in an amount of 500 to 50000 weight ppm with respect to the filament.

As the conjugated filaments comprising the low melting point resin as the first component and crystalline thermoplastic resin as the second component, the following conjugated filaments are preferably used: a core and sheath type conjugated filament comprising a low melting point resin of the first component as a sheath component and a crystalline thermoplastic resin of the second component as a core component; a so called an eccentric core and sheath type conjugated filament in which the location of the core component is eccentric in the cross section of the core and sheath type conjugated filament; and a so called parallel type conjugated filament (a side-by-side type conjugated filament) in which the low melting point component of the first component and the crystalline thermoplastic resin of the second component are adhered to each other. In particular, it is preferable that the eccentric core and sheath type conjugated filament or the parallel type conjugated filament are used, since crimped filaments can easily be obtained and the filament non-woven fabric having a high bulkiness and good hand feeling can be obtained. The ratio of the first component to the second component in the cross section of the parallel type conjugated filament may be 1:1 or, needless to say, the filament may have one component occupy a greater portion than the other component.

The volume ratio of the first component to the second component (corresponding to the area ratio in the cross section, if the cross section of the fiber is used) is usually in the range of 10:90 to 90:10 expressed as the ratio of the first component to the second component. More preferably, it is in the range of 30:70 to 30:70.

As the first component of the present invention, at least one kind of low melting point resin selected from the group consisting of olefin binary copolymer and olefin terpolymer is used. Herein, olefin binary copolymers may be used alone, olefin terpolymer may be used alone, the mixture in which olefin binary copolymer and olefin terpolymer are blended at an optional ratio may be used, or the mixture in which two or more different types of olefin binary copolymers are blended at an optional ratio may be used and moreover the mixture in which two or more different types of olefin terpolymers are blended at an optional ratio may be used. Since each can be used alone, the mixing ratio of olefin binary copolymer and olefin terpolymer, the mixing ratio of two ore more different kinds of olefin binary copolymers, and the mixing ratio of two or more different kinds of olefin terpolymers are not particularly limited and optionally determined. If the blending ratio is numerically expressed, assuming that, for example, two types of components are used; then 0 wt. %<a wt. %<100 wt. %, and b wt. %=100 wt. %−a wt. %, wherein a wt. % denotes the blending ratio of one component with respect to the total weight and b wt. % denotes the blending ratio of another component with respect to the total weight. In the case of using three or more components, similar to the above, the blending ratio of each component is optionally determined in the range of more than 0 wt. % and less than 100 wt. %, and the total ratio is 100 wt. %.

The first component that is used in the present invention, that is at least one low melting point resin selected from the group consisting of olefin binary copolymer or olefin terpolymer, is not limited as long as it is thermally melted or softened at a lower temperature than the second component, that is crystalline thermoplastic resin, and can exhibit thermal adhesion. It is preferable that the low melting point resin of the first component can thermally melted or softened at a temperature that is lower by not less than 5° C., more preferably by not less than 30° C. than the melting or softening temperature of the crystalline thermoplastic resin as the second component, since thermal damage to the physical properties of the second component is inhibited in a case where the resultant filament fleeces are thermally melted.

As specific examples of olefin binary copolymer and olefin terpolymer of the first component of the present invention, the following can be used: ethylene-propylene copolymer comprising 85 to 99 wt. % of propylene and 1 to 15 wt. % of ethylene; butene-propylene copolymer comprising 50 to 99 wt. % of propylene and 1 to 50 wt. % of 1-butene; ethylene-octene copolymer comprising 73 to 99 wt. % of ethylene and 1 to 27 wt. % of 1-octene (more preferably, ethylene-octene copolymer comprising 75 to 98 wt. % of ethylene and 2 to 25 wt. % of 1-octene); and ethylene-butene-propylene copolymer comprising 84 to 97 wt. % of propylene, 1 to 15 wt. % of 1-butene and 1 to 10 wt. % of ethylene. When the above mentioned copolymers are used, the softness unique to the copolymer can be exhibited. Moreover, as to crystallization of the resin when discharged from the spinning nozzle in the melting state, the apparent crystallization rate relatively increases by adding inorganic powder, and relatively many small crystals can be produced. However, this nucleating effect is relatively small, the increase in the crystallization temperature hardly occurs, and the increase in the crystallization is remarkably small. Consequently, the preferable filament non-woven fabric which is excellent in the hand feeling such as softness or touch etc. and is excellent in adhesion to the other members easily can be obtained, without damaging the properties such as softness or excellent adhesive property or low temperature adhesive property of the low melting point or low softening point olefin copolymer. Moreover, the time or distance (the solidification length) when filaments comprising the resin are crystallized and solidified does not become particularly long. Adding inorganic powders can expose inorganic powder to the surface of the filament and provides minute unevenness on the surface of the filament, which decrease the contacting area between filaments and prevent filaments from being adhered between filaments during spinning, so that filament breakage does not easily occur and thus the spinning property can be improved.

As the crystalline thermoplastic resin of the second component of the present invention, the crystalline thermoplastic resin that has higher melting point or higher softening point than that of the first component, that is at least one selected from the group consisting of olefin binary copolymer and olefin terpolymer, and that is capable of conjugate spinning together with the first component is used. As preferable examples, polypropylene or polyethylene terephthalate can be mentioned. It is preferable that propylene is used as the second component, since a relatively flexible filament non-woven fabric can be produced. Moreover, it is preferable that polyethylene terephthalate is used as the second component, since the filament non-woven fabric which has a greater strength and more excellent elasticity (cushion property) when crimps are provided can be obtained.

MFR (melt flow rate) of the resin that is used herein is not particularly limited, however, in a case where olefin resin is used, MFRs of both the first component and the second component are usually in the range of 10 to 100 g/10 min.

In addition, as a resin of the first component, the resin polymerized by the use of Ziegler-Natta catalyst or polymerized by the use of so called metallocene catalyst or the like can be used. In a case where the resin of the second component is olefin copolymer, the same is true.

As the inorganic powder used in the present invention, any type of inorganic powder can be used as long as it can provide unevenness to the surface of filament and prevent adhesion between filaments.

The particle diameter of the inorganic powder is preferably in the range of 0.04 to 2 μm in the average diameter, and more preferably it is in the range of 0.04 to 1 μm. If the inorganic powder whose particle diameter is too small is used, the cost becomes higher, clogging of filter or spinning nozzle occurs, or the filament breakage occurs to cause the deterioration in the operating efficiency because the secondary coagulation is easily generated. On the other hand, if the particle diameter is too large, dispersion of the inorganic powder is bad, clogging of the filter or spinning nozzle occurs, and the operating efficiency tends to be deteriorated due to the filament breakage. Consequently, the above mentioned range of the particle diameter is particularly preferred. The particle diameter of the inorganic powder can be measured by observation with an electron microscope.

For example, in a case where the particle diameter of the inorganic powder contained in the conjugated filament is measured, the conjugated filaments are heated under vacuum to separate the inorganic powder from the polymer constituting the conjugated filament, and then the particle diameter can be measured by the use of an electron microscope. At this time, in a case where the shape of the particle is different from a spherical shape, the particle diameter is determined by converting to the particle diameter of a spherical shaped particle having an equal volume to the observed particle.

As specific examples of the inorganic powder used in the present invention, a wide variety of stable and inactive inorganic powders can be used, for example, titanium dioxide, silica, alum, calcium carbonate, calcium oxide, magnesium oxide, talc etc. These inorganic powders can provide the minute unevenness to the surface of the conjugated filament. As a result, the adhesion between filaments during spinning can be prevented. Thus, in the filament non-woven fabric, for example, spun bond non-woven fabric or the like, as mentioned above, the non-uniformity of fineness or opening property is excellent and filament breakage is improved and operating efficiency is enhanced. Moreover, these inorganic powders have a relatively small nucleating property, so that the characteristics of low melting point or low softening point olefin copolymer, for example, softness, excellent adhesive property, low temperature adhesive properties etc., are not damaged and a filament non-woven fabric which is excellent in hand feeling such as softness or touch etc. and adhesion to the other members can be obtained. In particular, titanium dioxide, silica, alum, calcium carbonate, calcium oxide, magnesium oxide and talc are preferred since they have small nucleating properties. Pure types of the above mentioned inorganic powders may be used, however, the use of the pure type inorganic powder makes the cost higher. Therefore, inorganic powder including impurities may be used as long as the object of the present invention is not damaged. Moreover, in titanium dioxide, there are rutile type titanium dioxide and anatase type titanium dioxide and both can be used. However, from the view point of an excellent weatherability and heat resistance, the rutile type titanium dioxide is preferred. Moreover, the inorganic powder needs to be added into at least the first component and may be added into both the first and second components.

The inorganic powder may be introduced from a side feeder that is provided at an extruder and kneaded with melt-extrusion. In addition, the inorganic powder may be added in the form of a compound that is previously kneaded with, for example, the first component or in the form of masterbatch. When this inorganic powder is kneaded, in general, appropriate dispersing agents are used so as to enhance the dispersing property.

It is preferable that the content of inorganic powder contained in the filament is in the range of 500 to 50000 weight ppm. If the content of inorganic powder is too little, the adhesion preventing effect between filaments during spinning due to minute unevenness on the surface of the filament is not sufficiently exhibited, so that filaments form bundles by friction, thus causing the non-uniformity in the fineness or poor opening of filaments and deteriorating the operating efficiency due to filament breakage. If the content of the inorganic powder is too much, the clogging of the filter or spinning nozzle occurs, or operating efficiency tends to easily be deteriorated due to filament breakage. Therefore, the above mentioned range of the content is preferred. Moreover, in particular, in a case where the filament non-woven fabric of the present invention is used for sanitary napkins, it is preferable that the content of inorganic powder is not more than 12000 weight ppm in the total weight as a resin ash content.

As to the content of the inorganic powder, "the concentration with respect to the fibers" denotes, in the case of the conjugated fiber, the concentration with respect to the entire fiber. Therefore, even if inorganic powder is added only to the first component, the concentration denotes the average concentration of the entire conjugated fiber comprising the first component and the second component.

In the present invention, the fineness of the conjugated filament constituting the non-woven fabric is not particularly limited. The fineness is determined appropriately in accordance with the type of resin materials or intended use of the non-woven fabric. Preferably, the fineness is approximately 1 to 8 d/f. When being used for hygienic goods such as sanitary napkins, incontinence pads, operation cloth, surgical comforter having an opening for surgical site, base clothes for a cataplasm or the like, the fineness is preferably in the range of 1 to 5 d/f.

The basis weight of the filament non-woven fabric of the present invention also is not particularly limited. It may be determined appropriately in accordance with the types of the resin material to be used or the applications of the use. Preferably, the basis weight is approximately 10 to 50 g/m$^2$. In particular, in a case where the filament non-woven fabrics are used for sanitary materials, it is preferably about 10 to 30 g/m$^2$.

The filament non-woven fabric of the present invention can be produced by conjugated filaments spun out of a spinneret for melt spinning by the use of the above explained resin composition. However, such filament non-woven fabric easily can be produced by the well known spun bond method.

Since the spun bond method is well known, the detailed explanation will be omitted. For example, the spun bond non-woven fabric comprising filaments will be produced by the following manner: the mixture of at least one low melting point resin component selected from the group consisting of olefin binary copolymer and olefin terpolymer and an inorganic powder is prepared as the first component, and crystalline thermoplastic resin (if necessary, crystalline thermoplastic resin in which inorganic powder is mixed may be used) is prepared as the second component. These resin components are fed into the individual extruders and melted and spun by the use of the composite spinneret. A group of filaments discharged from the spinneret are introduced into an air sucker to be stretched by drawing to be formed into a group of filaments. Then, a group of filaments discharged out of the air sucker is electrically charged with the same electric charge by the use of an appropriate electrical charging apparatus such as corona discharging apparatus, and then are made to pass between a couple of vibrating wing-like tools (flaps) for an opening to open the filaments, or they are made to impact on an appropriate reflecting board etc. to open filaments. The groups of the opened filaments are accumulated as filament fleeces on an endless belt conveyor having a sucker on its back face. The collected filament fleeces are carried on the endless conveyor, introduced between the heated press rolls of the point bond processor comprising a heated embossing roll and smooth surface roll, and thereby the filament non-woven fabric in which the first component is melted or softened, and the filaments are thermally adhered is obtained at the portion corresponding to the convex portion of the embossing roll. The basis weight of the filaments non-woven fabric can be adjusted by adjusting the rate of the spinning discharging rate (discharging volume per hour) or the moving rate of the endless conveyor. Moreover, the formation method where the filament fleeces are formed into the filament non-woven fabric is not limited to the point bond method alone, and other methods, for example, hot air heating method, high pressure water stream method, needle punching method, ultrasonic heating method, or the like may be used. The combination of such methods for forming the non-woven fabric can be applied.

Moreover, the method for producing the filament non-woven fabric of the present invention is not limited to the above explained methods, however, the spun bond method is very preferable because the non-woven fabric which is excellent in the mechanical properties can easily be obtained, and the non-woven fabric can be obtained by opening and accumulating by the use of the filaments as it is obtained by the method of melt spinning, so that the productivity is very excellent.

The filament non-woven fabric of the present invention thus manufactured comprises the thermally adhesive conjugated filaments, so that the adhesive strength such as thermal adhesion and thermal compression bonding etc. is excellent. Filament non-woven fabrics comprising conjugated filaments that are excellent in the operating efficiency such as spinning properties can be obtained, so that they can be used for various applications and can be effectively used for the production of composite materials using this filament non-woven fabric.

Moreover, the filament non-woven fabric of the present invention can be used for at least one portion of the absorbent articles such as sanitary napkins, disposable diapers or the like.

Moreover, the absorbent articles such as disposable diapers like paper diapers, sanitary napkins and the like have structures so that body fluids such as urine, blood or the like are absorbed and leakage is prevented. Although the structure of such absorbent articles may differ somewhat between respective embodiments, however, such an absorbent article comprises at least an absorptive core layer for absorbing and retaining body fluids such as urine, blood or the like; a liquid permeable top sheet is produced from, for example, a non-woven fabric and located at the side of the front surface (the side contacting with the user's skin); and a liquid impermeable back sheet located at the back side that prevents the absorbed body fluids from leaking outside. Moreover, in general, in absorbent articles such as disposable diapers like paper diapers or sanitary napkins and the like, in addition to the back sheet, water repellent side sheets are provided at both sides of the absorbent articles so as to prevent absorbed liquid such as body fluids from leaking when the absorbent articles are displaced from the desired place due to the user's physical motion or when a user lays down on his/her side. (In the case of disposable diapers, since the water repellent side sheets are often provided with gathers, they are called a side gather or a leg cuff etc. In the case of disposable diapers, such side sheets are provided in a place that holds the joints of the thigh or the circumference of the thigh.) In addition, in the disposable diapers, a water-repellent round sheet that comprises a non-woven fabric or the like also is provided at the skin side of the portion covering the abdomen or the portion covering the upper buttock that is located opposite to the abdomen in order to prevent the leakage of liquids such as body fluids or the like, which are absorbed by the absorbent articles and which leak to the abdomen portion or the upper buttock portion from leaking outside of the absorbent articles when the user falls down or lays down or turns the body. Moreover, in the disposable diapers, a belt-like waist gather etc. is often provided in the waist portion. Such gathers also comprise a water repellent sheet such as a non-woven fabric or the like.

Moreover, for the core layer, various kinds of appropriate absorptive core layers are used. Such absorptive core layers comprise the compressed mixture in which an aggregate of fibers comprising cellulose type fiber such as fluff pulp etc. with which if necessary further synthetic fibers are mixed, and a high water absorptive resin are mixed and compressed to harden. This absorptive core layer is, in general, wrapped up by, for example, tissue paper. Moreover, as a back sheet, a thermoplastic film is usually used. The thermoplastic film has a large number of minute micropores so as to prevent stuffiness inside when worn and to provide ventilation. Moreover, from the viewpoint of improving the plastic-like touch and appearance which are peculiar to films, or from the viewpoint of improving the strength, the composite comprising a film and a non-woven fabric is also used. In addition, in order to provide various kinds of functions, there are absorbent articles comprising additional layers to which the other sheets are inserted further.

The filament non-woven fabric of the present invention can be used for the top sheet, side sheet, round sheet, and a part of the back sheet (the laminate with liquid impermeable sheet or the like) depending on the respective objects. Moreover, the necessary portion between these members is appropriately thermally adhered and fixed.

Moreover, for the adhesion by means of thermal pressure or thermal adhesion between these members, partial point adhesion capable of multiple-point adhesion is usually preferably employed, although it varies depending on the portion to be used.

Hereinafter, the places of the absorbent article in which the filament non-woven fabric of the present invention is used will be explained as follows with reference to the figures. However, the structures of the absorbent article shown here are just one embodiment and the absorbent articles are not limited to the absorbent articles having a structure shown herein.

Figure 2:
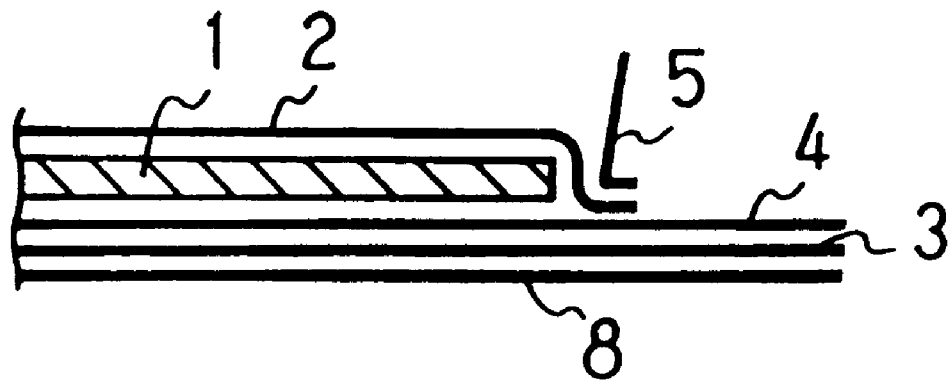
FIG. 2 is a schematic end view taken on line X-X' of FIG. 1.

FIG. 1 is a plan view showing one embodiment of the disposable diaper when viewed from the side of the user's skin; FIG. 2 is a schematic end view taken on the line X-X'; and FIG. 3 is a schematic end view taken on the line Y-Y'.

Figure 3:
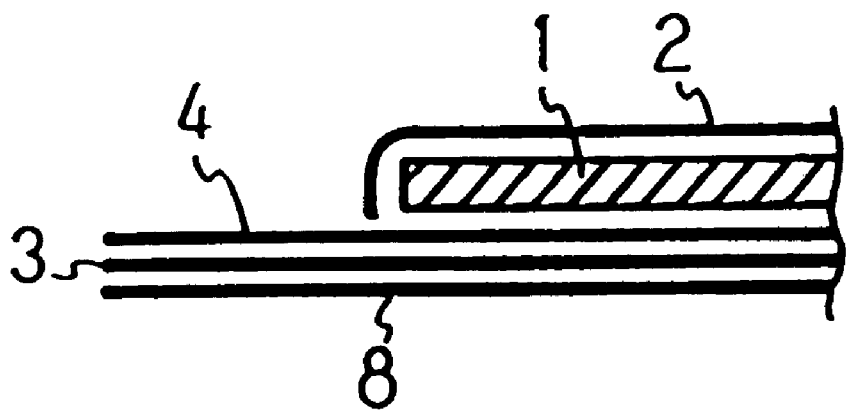
FIG. 3 is a schematic end view taken on line Y-Y' of FIG. 1.

In FIG. 1 to FIG. 3, numeral 1 denotes an absorptive core layer for absorbing and retaining body fluids. It is not particularly limited, but it comprises the compressed mixture in which cellulose fiber such as fluff pulp, high water absorptive resin and, if necessary, synthetic fiber are compressed to harden. Moreover, the absorptive core layer 1 is wrapped up by, for example, tissue paper (not shown). Numeral 2 denotes a liquid permeable top sheet that is located at the front surface side thereof (the side contacting with the user's skin). The filament non-woven fabric of the present invention can be used for this top sheet 2. Numeral 3 denotes a back sheet that requires water impermeability. For covering the surface of the back sheet 3, the filament non-woven fabric of the present invention can be laminated as the back sheet laminate 8. When the filament non-woven fabric of the present invention is laminated to the back sheet of such absorbent articles; the cool touch of plastic film or an appearance peculiar to plastic film is improved, a warm cloth-like touch and an appearance can be provided, and at the same time, the back sheet can be reinforced.

A round sheet 4 is not always necessary, in FIG. 2 and FIG. 3, the round sheet 4 is located between the absorptive core layer 1 and the back sheet 3. The filament non-woven of the present invention also can be used for the round sheet 4. And 5 and 5' denote the side sheets and they are provided at both sides of the absorbent articles so as to prevent absorbed liquid such as body fluids from leaking when the absorbent articles are displaced from the desired place due to the user's physical motion or when a user lays down on his/her side. (In the case of disposable diapers, since the water repellent side sheets often are provided with gathers, they are called a side gather or a leg cuff etc. In the case of disposable diapers, such side sheets are provided in a place that holds the joints of the thigh or the circumference of the thigh.) For this side sheet, the filament non-woven fabric of the present invention also can be used. Moreover, although not shown in FIG. 2 and FIG. 3, as shown in numeral 7 in FIG. 1, a belt like waist gather or the like may be provided at the skin side of the waist portion. The filament non-woven fabric of the present invention also can be used for the waist gather.

Each of these members is designed not to be dropped off by being adhered with hot melt type adhesive or thermally adhered or adhered by means of ultrasonic adhesion without using the adhesives (not shown in figures). In the disposable diapers of the present invention, the portion where the filament non-woven fabric of the present invention is used can be thermally adhered or adhered by means of ultrasonic energy without using adhesive.

Moreover, in disposable diapers, the filament non-woven fabric of the present invention need not to be used in every member explained above and may be used in one or more portions.

Figure 4:
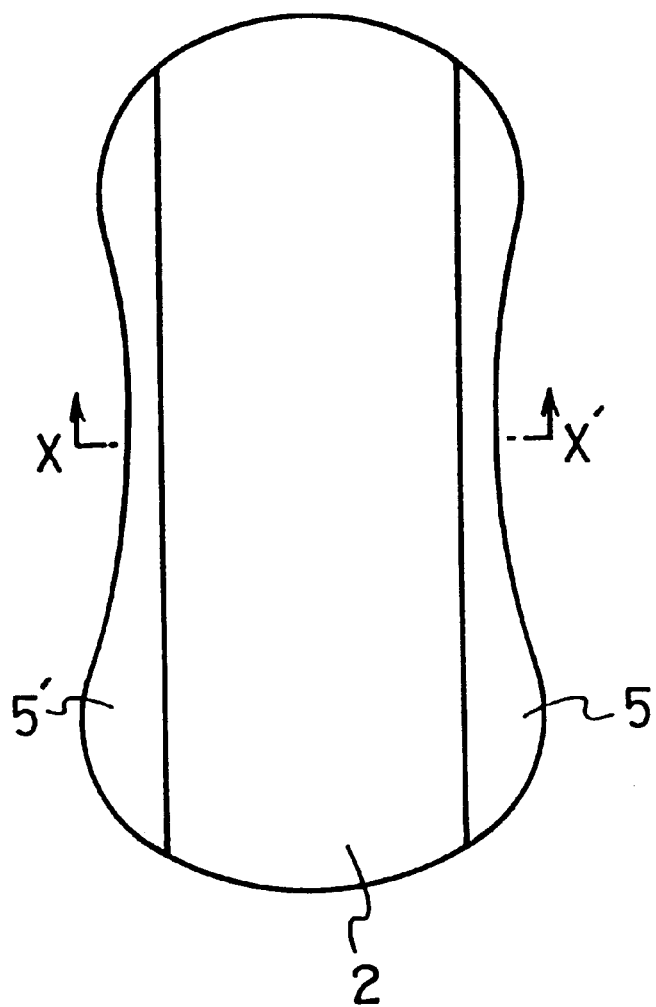
FIG. 4 is a plan view of one embodiment of the sanitary napkin using the filament non-woven fabric of the present invention in one part of it when viewed from the side of the user's skin.
Figure 5:
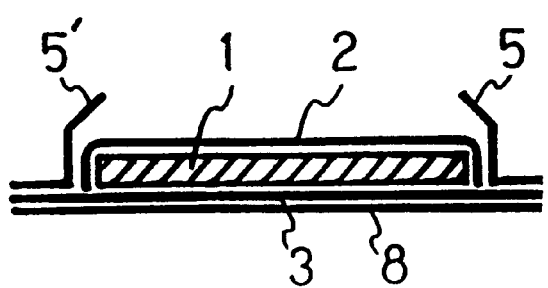
FIG. 5 is a schematic end view taken on line X-X' of FIG. 4.

Next, FIG. 4 is a plan view showing one embodiment of the sanitary napkins, when viewed from the skin side. Moreover, FIG. 5 shows a schematic end view taken on the line X-X'. Numeral 1 denotes an absorptive core layer wrapped up by tissue paper (not shown); 2 denotes a liquid permeable top sheet located at the front surface thereof (the side contacting with the skin); 3 denotes a back sheet that requires liquid impermeability; and 5 and 5' denote side sheets. To the backside of the back sheet 3, the filament non-woven fabric of the present invention can be laminated as the back sheet laminate 8. Moreover, the filament non-woven fabric of the present invention also can be used for the side sheets 5 and 5'.

Each of these members is designed not to be dropped off by being adhered with hot melt type adhesive or thermally adhered or adhered by means of ultrasonic adhesion without using the adhesives (not shown in figures). Moreover, in the sanitary napkins of the present invention, the portion where the filament non-woven fabric of the present invention is used can be thermally adhered or adhered by means of ultrasonic adhesion without using the adhesives.

Needless to say, similar to the above, in the above mentioned absorbent articles, the portion where the filament non-woven fabric of the present invention is used need not to be used in every member explained above and may be used in one or more portions.

The absorbent articles using the filaments non-woven fabric of the present invention is excellent in the resistance of the abrasion, strength of the non-woven fabric and hand feeling.

Hereinafter, the invention will be explained with reference to Examples and Comparative Examples, but is not limited to them alone.

EXAMPLES 1 TO 33 AND COMPARATIVE EXAMPLES 1 TO 5

The mixture comprising one copolymer or the mixture of two or more copolymers selected from the group consisting of olefin binary copolymer or olefin terpolymer having qualities shown in Table 1 to 3 (and Table 4 regarding Comparative Examples) and inorganic powder shown in each Table was prepared as the first component. Moreover, the content of inorganics was shown by the use of the concentration with respect to fibers which was previously defined. Therefore, the concentrations of inorganic powder contained only in the first component are higher than the concentrations shown in Tables. (The concentration of the inorganic powder contained only in the first component can easily be calculated from the concentration with respect to the fibers and conjugation ratio.) Moreover, as the second component, crystalline thermoplastic resins having the qualities shown in Tables 1 to 4 were prepared. Moreover, in Comparative Example 5, a single fiber comprising only the second component, that is, a single fiber comprising polypropylene was used. These resin compositions were respectively fed into the separate extruders of 60 mm φ and extruded in a way in which the total volume of the both components was made to be at the rate of 2200 cc/min in accordance with the conjugation ratio of the first component to the second component (specifically, in a case where the conjugation ratio A/B of the first component (A) to the second component (B) was 50/50, the extruding ratio of the first component was 1100 cc/min, and the extruding ratio of the second component was 1100 cc/min). Each composition was extruded at the following extruding temperatures: in a case where the second component was polypropylene and the main component of the monomer component constituting the first component of the olefin copolymer is propylene, the extruding temperature was 250° C. (in the case of Comparative Example 5, the extruding temperature was also 250° C.); in a case where the second component was polypropylene and the main component of the monomer component constituting the first component of the olefin copolymer was ethylene, the temperature was 230° C.; and in a case where the second component was polyethylene terephthalate, the temperature was 280° C. For melt spinning, as shown in the column of conjugation types of Tables, various types of spinnerets, that is, parallel type, core and sheath type or eccentric core and sheath type, were respectively used. As the spinneret, the spinneret having circular spinning holes of 0.35 mm hole diameter arranged in 550 holes×5 columns in the longitudinal direction of the spinneret was used. The group of fibers discharged from the spinneret was introduced into an air sucker to be stretched by drawing, to thus produce the group of filaments. And then, a group of filaments discharged from the air sucker was electrically charged with the same electric charge with a corona discharging apparatus, and made to pass through between a couple of vibrating wing-like tools to open filaments. A group of the opened filaments was collected as filaments fleece on the endless net conveyor having suckers on its back surface. At this time, the stretching speed by the air sucker was controlled in accordance with the type of fibers so as to adjust the fineness of the filaments to be appropriately 2.2 d/f. Moreover, the concentration of the inorganic powder in the fiber was as shown in Table. The collected filament fleece was carried on the endless conveyor and introduced between the press rolls of a point bond processor comprising a heated embossing roll and a smooth surface roll. The introduced filament fleece was formed into the filament non-woven fabric in which the filaments were thermally melt adhered by the first component melting or softening at the portion corresponding to the convex part of the embossing roll. The basis weight of the filament non-woven fabric was controlled to 28 g/m$^2$ by adjusting the moving speed of the endless conveyor around 50 m/min in accordance with the types of fibers. Moreover, the peripheral velocity of the embossing rolls was made to be the same as the moving speed of the endless conveyor. The linear load between rolls and roll temperature were appropriately set in a way in which the average value of the longitudinal direction and vertical direction of bending resistance (under the condition specified in JIS L 1096 A, 45° cantilever method, wherein the size of the sample was 5 cm×15 cm) of the filament non-woven fabric was made to be about 30 mm.

Moreover, in Examples, every formation of the non-woven fabric (thermal adhesion between filaments) was conducted by the point bond method for conforming the conditions at the time of the sensory analysis. The method of producing the non-woven fabric may be a hot air heating method, high water pressure method, needle punching method, ultrasonic heating method and a combination of the plurality of the above methods.

In a case where polyethylene terephthalate was used as the second component, polyethylene terephthalate having an IV (intrinsic viscosity) of 0.64 was used. The measurement of the IV value was conducted by the use of the mixture comprising an equal amount of phenol and ethane tetrachloride as a solvent at 20° C.

Moreover, the average particle diameters of inorganics shown in Tables 1 to 4 were: the average particle diameter of silica was 0.04 μm; TiO$_2$ was 0.20 μm; alum was 0.95 μm; CaCo$_3$ was 0.08 μm; CaO was 0.35 μm; MgO was 0.17 μm; and talc was 0.40 μm. Moreover, as TiO$_2$, rutile type titanium dioxide was used. In addition, the content rate ppm denotes weight ppm; PP as the second component denotes polypropylene; and PET as the second component denotes polyethylene terephthalate. As to the volume ratio A/B written in the column of the conjugating ratio, A denotes the first component, B denotes the second component and the entire value of the conjugated fiber was 100.

As to "the mixing ratio" in the column of the first component (A) in Tables 1 to 4, in a case where a value was written in the column of the mixing ratio, the first component is formed by blending two kinds of resins. The value in the column of the mixing ratio shows the mixing ratio (wt. %) of the resin component whose value was written when the entire resin used for the first component was made to be 100 wt. %. Therefore, another component of the first resin component was the remainder. If the value was not written in the column of the mixing ratio in Table, the used amount of the component was 0 wt. %, and therefore another component written in Table was used at 100 wt. % (in other words, another component was used alone) as the first resin component.

The evaluation results of the filament non-woven fabrics obtained in the above mentioned manner were shown in Tables 5 to 9.

Moreover, the measurement method of each evaluation item and evaluation standard are as follows.

(MFR)

MFR was measured under the condition 14 of Table 1 specified in JIS K 7210.

(Tensile Strength)

Tensile test by Tensilon tensile tester was carried out under the condition specified in JIS L 1096. After the tensile strength of the longitudinal direction and that of the lateral direction were measured, the measured value was divided by the basis weight and the width of the sample to make the tensile strength of the longitudinal direction and the lateral direction. The value was substituted in the following equation and the tensile strength was calculated: (tensile strength of the longitudinal direction×tensile strength of the vertical direction )$^{1/2}$. Herein, the longitudinal direction denotes, the direction in which filament was carried on the endless conveyor, or the so-called the mechanical direction. And the lateral direction denotes the direction perpendicular to the longitudinal direction.

(Bending Resistance)

Bending resistance was measured by the 45° cantilever method under the conditions specified in JIS L 1096 A. Bending resistance of the longitudinal direction and the transverse direction were measured and the average value thereof was calculated. Moreover, the size of the sample was made to be 5 cm×15 cm.

(Uniformity Index of Filament Non-woven Fabric)

Five 5×5 cm samples were taken out from the non-woven fabric at equal intervals in the transverse direction, and cut into 1×1 cm pieces and their weights were measured. Each of five samples was calculated by the following equation to calculate the average value of five samples: ((the maximum value)−(the minimum value))×100/(the average value). The value was used as the parameters of non-uniformity of opening or non-uniformity of fineness. The smaller this value is, the more uniform the non-woven fabric is. When this value is not more than 80, the non-woven fabric may be thought to be excellent in uniformity.

(Touch)

The sensory test was carried out by 10 monitors. They directly touch the surface of the filament non-woven fabric and evaluate it by marking 1 point when they feel that it had a good touch.

(Softness)

The sensory test was carried out by 10 monitors. They directly grasp the filament non-woven fabric and evaluate it by marking 1 point when they feel that it had a good softness.

(Spinning Property)

The number of occurrences of filament breakage during 3-hour melt spinning was measured. If it is not more than 3 times, the spinning property may be thought to be good.

TABLE 1

| | First Component (A) | | | | | | | | | | | Second Component (B) | | Com- posing Ratio Volume Ratio A/B | Conju- gating Type *2 |
|---|---|---|---|---|---|---|---|---|---|---|---|---|---|---|---|
| | Ethylene - butene - propylene Copolymer | | | | Binary Component | | | | | | Inorganic Substance | | | | |
| | Ethy- lene Part wt. % | 1- butene part wt. % | MFR g/10 min | Melting Point ° C. | Main Com- ponent | Co- monomer Com- ponent | Co- mono- mer Part wt. % | MFR g/10 min | Melt- ing Point ° C. | Blend -ing Ratio % | Addi- tive Type | Con- tent *1 | Resin | MFR g/10 min | | |
| Ex. 1 | 2.5 | 4.5 | 33 | 142 | — | — | — | — | — | — | silica | 1000 | PP | 35 | 50/50 | P |
| Ex. 2 | 8.0 | 4.0 | 41 | 134 | — | — | — | — | — | — | TiO$_2$ | 10000 | PP | 35 | 60/40 | C&S |
| Ex. 3 | 13.2 | 1.1 | 36 | 131 | — | — | — | — | — | — | alum | 15000 | PET | — | 40/60 | E C&S |
| Ex. 4 | 8.0 | 5.2 | 29 | 129 | — | — | — | — | — | — | CaCO$_3$ | 35000 | PET | — | 50/50 | C&S |
| Ex. 5 | — | — | — | — | propylene | ethylene | 1.9 | 36 | 156 | 100 | CaO | 500 | PP | 35 | 20/80 | P |
| Ex. 6 | — | — | — | — | propylene | ethylene | 5.2 | 44 | 141 | 100 | TiO$_2$ | 15000 | PP | 35 | 70/30 | C&S |
| Ex. 7 | — | — | — | — | propylene | ethylene | 6.1 | 31 | 132 | 100 | MgO | 8000 | PET | — | 40/60 | E C&S |
| Ex. 8 | — | — | — | — | propylene | ethylene | 11.8 | 28 | 119 | 100 | CaCO$_3$ | 30000 | PET | — | 50/50 | C&S |
| Ex. 9 | — | — | — | — | ethylene | 1-octene | 18.7 | 32 | 86 | 100 | CaO | 500 | PET | — | 50/50 | C&S |
| Ex. 10 | — | — | — | — | ethylene | 1-octene | 13.4 | 28 | 100 | 100 | TiO$_3$ | 15000 | PP | 35 | 20/80 | P |
| Ex. 11 | — | — | — | — | ethylene | 1-octene | 9.5 | 35 | 103 | 100 | MgO | 8000 | PP | 35 | 70/30 | C&S |
| Ex. 12 | — | — | — | — | ethylene | 1-octene | 2.0 | 36 | 121 | 100 | CaCO$_3$ | 30000 | PET | — | 40/60 | E C&S |
| Ex. 13 | — | — | — | — | ethylene | 1-octene | 25 | 40 | 54 | 100 | alum | 15000 | PET | — | 40/60 | E C&S |
| Ex. 14 | — | — | — | — | ethylene | 1-octene | 7.5 | 25 | 108 | 100 | CaCO$_3$ | 35000 | PET | — | 50/50 | C&S |
| Ex. 15 | — | — | — | — | propylene | 1-butene | 20.1 | 40 | 130 | 100 | CaO | 500 | PP | 35 | 20/80 | P |

TABLE 2

| | First Component (A) | | | | | | | | | | | Second Component (B) | | Com-posing Ratio Volume Ratio A/B | Conju-gating Type *2 |
|---|---|---|---|---|---|---|---|---|---|---|---|---|---|---|---|
| | Ethylene - butene - propylene Copolymer | | | | Binary Component | | | | | | Inorganic Substance Additive | | | | |
| | Ethylene Part wt. % | 1-butene wt. % | MFR g/10 min | Melting Point ° C. | Co-monomer Main Component | Co-monomer Component | Co-monomer Part wt. % | MFR g/10 min | Melting Point ° C. | Blending Ratio % | type | Content *1 | Resin | MFR g/10 min | | |
| Ex. 16 | 8.0 | 5.2 | 29 | 129 | propylene | ethylene | 11.8 | 28 | 119 | 10 | talc | 500 | PP | 35 | 50/50 | C&S |
| Ex. 17 | 8.0 | 5.2 | 29 | 129 | propylene | ethylene | 5.2 | 44 | 141 | 50 | TiO$_2$ | 15000 | PP | 35 | 60/40 | E.C&S |
| Ex. 18 | 8.0 | 5.2 | 29 | 129 | propylene | ethylene | 6.1 | 31 | 132 | 90 | CaCO$_2$ | 2500 | PET | — | 40/60 | C&S |
| Ex. 19 | 8.0 | 5.2 | 29 | 129 | ethylene | 1-octene | 18.7 | 32 | 86 | 10 | CaCO$_3$ | 30000 | PET | — | 50/50 | C&S |
| Ex. 20 | 8.0 | 5.2 | 29 | 129 | ethylene | 1-octene | 25 | 40 | 54 | 50 | CaO | 500 | PP | — | 50/50 | C&S |
| Ex. 21 | 8.0 | 5.2 | 29 | 129 | ethylene | 1-octene | 9.5 | 35 | 103 | 90 | TiO$_2$ | 15000 | PP | 35 | 20/80 | P |
| Ex. 22 | 8.0 | 5.2 | 29 | 129 | propylene | 1-butene | 20.1 | 40 | 130 | 10 | CaO | 500 | PP | 35 | 30/60 | P |
| Ex. 23 | 8.0 | 5.2 | 29 | 129 | propylene | 1-butene | 20.1 | 40 | 130 | 50 | TiO$_2$ | 15000 | PP | 35 | 70/30 | C&S |
| Ex. 24 | 8.0 | 5.2 | 29 | 129 | propylene | 1-butene | 20.1 | 40 | 130 | 90 | CnCO$_2$ | 2500 | PET | — | 40/60 | E.C&S |

TABLE 3

| | First Component (A) | | | | | | | | | | | Second Component (B) | | Com-posing Ratio Volume ratio A/B | Conju-gating Type *2 |
|---|---|---|---|---|---|---|---|---|---|---|---|---|---|---|---|
| | Binary Component | | | | Binary Component | | | | | | Inorganic Substance Additive | | | | |
| | Main Component | Co-monomer Component | 1-butene wt. % | MFR g/10 min | Melting point ° C. | Main Component | Co-monomer Component | Co-monomer Component | part wt. % | MFR g/10 min | Melting Point ° C. | Blending ratio % | type | Content *1 | Resin | MFR g/10 min |
| Ex. 25 | propylene | ethylene | 5.2 | 44 | 141 | ethylene | 1-octene | 18.7 | 32 | 86 | 10 | talc | 500 | PP | 85 | 50/50 | C&S |
| Ex. 26 | propylene | ethylene | 5.2 | 44 | 141 | ethylene | 1-octene | 25 | 40 | 54 | 50 | TiO$_2$ | 15000 | PP | 35 | 60/40 | E.C&S |
| Ex. 27 | propylene | ethylene | 5.2 | 44 | 141 | ethylene | 1-octene | 9.5 | 35 | 103 | 90 | CaCO$_3$ | 2500 | PET | — | 40/60 | C&S |
| Ex. 28 | propylene | ethylene | 5.2 | 44 | 141 | propylene | 1-butene | 20.1 | 40 | 130 | 10 | CaCO$_3$ | 30000 | PET | — | 50/50 | C&S |
| Ex. 29 | propylene | ethylene | 5.2 | 44 | 141 | propylene | 1-butene | 20.1 | 40 | 130 | 50 | CaO | 500 | PET | — | 50/50 | C&S |
| Ex. 30 | propylene | ethylene | 5.2 | 44 | 141 | propylene | 1-butene | 20.1 | 40 | 130 | 90 | TiO$_2$ | 15000 | PP | 35 | 20/80 | P |
| Ex. 31 | propylene | 1-octene | 20.1 | 40 | 130 | Ethylene | 1-octene | 18.7 | 32 | 86 | 10 | CaO | 500 | PP | 35 | 30/70 | P |
| Ex. 32 | propylene | 1-octene | 20.1 | 40 | 130 | ethylene | 1-octene | 25 | 40 | 54 | 50 | TiO$_2$ | 15000 | PP | 35 | 70/30 | C&S |
| Ex. 33 | propylene | 1-octene | 20.1 | 40 | 130 | ethylene | 1-octene | 9.5 | 35 | 103 | 90 | CaCO$_2$ | 2500 | PET | — | 40/60 | E.C&S |

TABLE 4

| | First Component (A) | | | | | | | | | | Inorganic Substance | | Second Component (B) | | Com-posing | |
|---|---|---|---|---|---|---|---|---|---|---|---|---|---|---|---|---|
| | Ethylene - butene - propylene Copolymer | | | | Binary Component | | | | | | Additive | | | | Ratio | Conju-gating |
| | | | | | | Co-monomer | Co-mono- | | Melt- | Blend | | | | | | |
| | Ethy-lene | 1-butene | MFR | Melting | Main Com- | Com- | mer | MFR | ing | -ing | | Con- | | MFR | Vol. | gating |
| unit | Part wt. % | Part wt. % | g/10 min | Point ° C. | ponent — | ponent — | Part wt. % | g/10 min | Point ° C. | Ratio % | Type | tent *1 | Resin — | g/10 min | ratio A/B | Type *2 |
| Comp. Ex. 1 | 13.2 | 1.1 | 36 | 131 | — | — | — | — | — | — | TiO$_2$ | 350 | PET | — | 40/60 | E.C&S |
| Comp. Ex. 2 | — | — | — | — | propylene | ethylene | 6.1 | 31 | 132 | 100 | — | — | PET | — | 40/60 | E.C&S |
| Comp. Ex. 3 | — | — | — | — | ethylene | 1-octene | 13.4 | 28 | 100 | 100 | — | — | PP | 35 | 60/40 | C&S |
| Comp. Ex. 4 | — | — | — | — | propylene | 1-butene | 20.1 | 40 | 130 | 100 | — | — | PP | 35 | 20/80 | C&S |
| Comp. Ex. 5 | Polypropylene (MFR: 35 g/10 min.) | | | | | | | | | | | | | | | Single Fiber |

*1: Content of the inorganic powder (weight ppm) in the concentration with respect to filament.
*2: Each mark of conjugating type represents: C&S denotes core and sheath type conjugated filament composite; E.C&S denotes eccentric core and sheath type conjugated filament composite; and P denotes parallel type conjugated filament composite.

TABLE 5

| Unit | Tensile strength Kg/cm · (g/m$^2$) | Bending resis-tance mm | Uniformity index of filament non-woven fabric — | Touch point | Soft-ness point | Spinning property Times |
|---|---|---|---|---|---|---|
| Example 1 | 0.030 | 29 | 68 | 10 | 9 | 0 |
| Example 2 | 0.034 | 31 | 70 | 9 | 10 | 0 |
| Example 3 | 0.036 | 32 | 65 | 8 | 9 | 3 |
| Example 4 | 0.032 | 28 | 65 | 10 | 8 | 0 |
| Example 5 | 0.027 | 30 | 61 | 9 | 8 | 0 |
| Example 6 | 0.024 | 30 | 70 | 9 | 8 | 1 |
| Example 7 | 0.031 | 31 | 72 | 9 | 8 | 1 |

TABLE 6

| Unit | Tensile strength Kg/cm · (g/m$^2$) | Bending resis-tance mm | Uniformity index of filament non-woven fabric — | Touch point | Soft-ness point | Spinning property Times |
|---|---|---|---|---|---|---|
| Example 8 | 0.034 | 29 | 64 | 8 | 8 | 0 |
| Example 9 | 0.033 | 30 | 77 | 8 | 7 | 3 |
| Example 10 | 0.028 | 28 | 62 | 10 | 10 | 0 |
| Example 11 | 0.027 | 27 | 74 | 8 | 10 | 1 |
| Example 12 | 0.029 | 32 | 68 | 10 | 9 | 0 |
| Example 13 | 0.031 | 28 | 69 | 9 | 9 | 0 |
| Example 14 | 0.032 | 29 | 63 | 9 | 8 | 0 |
| Example 15 | 0.034 | 29 | 61 | 8 | 10 | 0 |

TABLE 7

| Unit | Tensile strength Kg/cm · (g/m$^2$) | Bending resis-tance mm | Uniformity index of filament non-woven fabric — | Touch point | Soft-ness point | Spinning property Times |
|---|---|---|---|---|---|---|
| Example 16 | 0.034 | 32 | 70 | 7 | 9 | 3 |
| Example 17 | 0.029 | 28 | 68 | 9 | 8 | 0 |
| Example 18 | 0.032 | 30 | 69 | 9 | 8 | 0 |
| Example 19 | 0.034 | 31 | 65 | 10 | 9 | 0 |
| Example 20 | 0.034 | 29 | 70 | 7 | 8 | 2 |
| Example 21 | 0.026 | 32 | 71 | 9 | 8 | 0 |
| Example 22 | 0.028 | 28 | 72 | 8 | 8 | 2 |
| Example 23 | 0.032 | 29 | 64 | 9 | 9 | 1 |
| Example 24 | 0.032 | 29 | 77 | 8 | 8 | 0 |

TABLE 8

| Unit | Tensile strength Kg/cm · (g/m$^2$) | Bending resis-tance mm | Uniformity index of filament non-woven fabric — | Touch point | Soft-ness point | Spinning property Times |
|---|---|---|---|---|---|---|
| Example 25 | 0.031 | 32 | 73 | 7 | 8 | 1 |
| Example 26 | 0.032 | 28 | 72 | 8 | 9 | 0 |
| Example 27 | 0.033 | 30 | 65 | 10 | 8 | 0 |
| Example 28 | 0.032 | 31 | 60 | 10 | 9 | 0 |

TABLE 8-continued

| Unit | Tensile strength Kg/cm · (g/m²) | Bending resis- tance mm | Uniformity index of filament non-woven fabric — | Touch point | Soft- ness point | Spinning property Times |
|---|---|---|---|---|---|---|
| Example 29 | 0.032 | 29 | 73 | 7 | 8 | 3 |
| Example 30 | 0.026 | 32 | 70 | 10 | 10 | 0 |
| Example 31 | 0.028 | 28 | 72 | 7 | 8 | 2 |
| Example 32 | 0.034 | 29 | 64 | 9 | 9 | 0 |
| Example 33 | 0.031 | 29 | 63 | 9 | 8 | 0 |

TABLE 9

| Unit | Tensile strength Kg/cm · (g/m²) | Bending resis- tance mm | Uniformity index of filament non-woven fabric — | Touch Point | Soft- ness Point | Spinning property Times |
|---|---|---|---|---|---|---|
| Comparative Example 1 | 0.031 | 30 | 83 | 3 | 6 | 5 |
| Comparative Example 2 | 0.032 | 29 | 110 | 3 | 5 | 7 |
| Comparative Example 3 | 0.029 | 31 | 122 | 3 | 6 | 11 |
| Comparative Example 4 | 0.028 | 29 | 90 | 3 | 7 | 5 |
| Comparative Example 5 | 0.030 | 30 | 61 | 5 | 5 | 0 |

A disposable diaper was made in which the back sheet 3 made of linear low density polyethylene stretched film, the back sheet laminate 8, the round sheet 4, the absorptive core layer 1 comprising fluff pulp and high absorptive resin wrapped up by the tissue paper cover, and the top sheet 2 comprising a non-woven fabric comprising sheath and core type conjugated staple fibers comprising high density polyethylene as a sheath component and polypropylene as a core component and being thermally adhered by the hot air heating method, were laminated in this order and joined, followed by positioning the side sheet 5, which comprised the laminate comprising spun bond non-woven fabric and melt blow non-woven fabric, in a way in which the side sheet 5 was overlapped at the edge portion of the longitudinal direction of the top sheet 2. Herein, as the back sheet laminate 8 and round sheet 4, the filament non-woven fabric of the present invention obtained in Examples 1 to 9 were used.

At this time, the back sheet 3 and the back sheet laminate 8, and between the back sheet 3 and the round sheet 4 were respectively adhered to be laminated by the dot-like thermal compression bonding. Moreover, the round sheet 4, the top sheet 2 and the side sheet 5 were thermal compressively bonded at the portion where the three sheets were overlapped.

The resultant disposable diapers were subjected to the wearing test. Since the non-woven fabric of the present invention was used as the back sheet laminate 8, a cool touch or appearance of the plastic film peculiar to plastic were improved and a warm cloth-like touch and appearance could be provided and the back sheet could be reinforced. Moreover, in the hand feeling such as softness or touch or the like is excellent. Adhesion between the top sheet 2 and round sheet 4, between the round sheet 4 and back sheet 3, and between the back sheet 3 and back sheet laminate 8 were good without using, for example, hot melt type adhesive etc, so that each layer was not peeled apart and the layer structure was not broken.

INDUSTRIAL APPLICABILITY

The filament non-woven fabric of the present invention can provide a filament non-woven fabric comprising the conjugated filaments, where the defects of the conventional filament non-woven fabrics are improved, high adhesive property and low temperature adhesive property are good, the resultant non-woven fabric has an excellent hand feeling such as softness or touch etc., the uniformity of the non-woven fabric is excellent, and the operating efficiency such as spinning property etc. also is good. The industrial utilization value of the filament non-woven fabric of the present invention is extremely high. In other words, by adding inorganic powder into the first component, namely, at least one low melting point or low softening point component, a filament non-woven fabric can be obtained in which the inorganic powder is exposed at the surface of the filaments, minute unevenness is provided on the surface of the filaments, adhesion between filaments during spinning can be prevented, the filament breakage is decreased, and the operating efficiency is made to be good. Furthermore, the nucleating effect of the inorganic powder is relatively small and the crystallization temperature of olefin copolymer hardly increases, so that the increase in the crystallization is remarkably small. Thus, the filament non-woven fabric is excellent in the hand feeling such as softness or touch etc. and can be well adhered to the other members, without damaging the properties, for example, softness, excellent adhesion properties, low temperature adhesion properties etc. of the low melting point or low softening point olefin copolymer.

Moreover, in the filament non-woven fabric of the present invention, by the preferred embodiment wherein the olefin terpolymer is ethylene-butene-propylene copolymer comprising 84 to 97 wt. % of propylene, 1 to 15 wt. % of 1-butene and 1 to 10 wt. % of ethylene, preferably, the filament non-woven fabric of the present invention can be provided in which the softness unique to copolymers can be exhibited. The conjugated filaments are not easily bundled by exposing inorganic powder on the surface of the filaments and providing minute unevenness on the surface of the filaments, so that the non-uniformity of the fineness of the filament is small and the opening property is excellent, and the filaments do not break easily and the spinning properties are improved.

Moreover, in the filament non-woven fabric of the present invention, by the preferred embodiment wherein the olefin binary copolymer is ethylene-propylene copolymer comprising 85 to 99 wt. % of propylene and 1 to 15 wt. % of ethylene, preferably, the filament non-woven fabric of the present invention can be provided in which the softness unique to copolymers can be exhibited. The conjugated filaments are not easily bundled by exposing inorganic powder on the surface of the filaments and providing minute unevenness on the surface of the filaments, so that the non-uniformity of the fineness of the filament is small and the opening property is excellent, and the filaments do not break easily and the spinning properties are improved.

Moreover, in the filament non-woven fabric of the present invention, by the preferred embodiment wherein the olefin binary copolymer is butene-propylene copolymer comprising 50 to 99 wt. % of propylene and 1 to 50 wt. % of 1-butene, preferably, the filament non-woven fabric of the present invention can be provided in which the softness unique to copolymers can be exhibited. The conjugated filaments are not easily be bundled by exposing inorganic powder on the surface of the filaments and providing minute unevenness on the surface of the filaments, so that the non-uniformity of the fineness of the filament is small and the opening property is excellent, and the filaments do not break easily and the spinning properties are improved.

Moreover, in the filament non-woven fabric of the present invention, by the preferred embodiment wherein the olefin binary copolymer is ethylene-octene copolymer comprising 73 to 99 wt. % of ethylene and 1 to 27 wt. % of 1-octene, preferably, the filament non-woven fabric of the present invention can be provided in which the softness unique to copolymers can be exhibited. The conjugated filaments are not easily bundled by exposing inorganic powder on the surface of the filaments and providing minute unevenness on the surface of the fibers, so that the non-uniformity of the fineness of the filaments is small and the opening property is excellent, and the filaments do not break easily and the spinning properties are improved.

Moreover, in the non-woven fabric of the present invention, it is preferable that the particle diameter of the inorganic powder is in the range of 0.04 to 2 $\mu$m. When compared with the case where inorganic powder has a smaller particle diameter, the cost is less increased, the secondary coagulation of inorganic powder or clogging in the filter or the spinning nozzle does not occur, and the operating efficiency is not deteriorated due to breakage. When compared with the case where the inorganic powder has a larger particle diameter, there is no fear that the dispersion of inorganic powder is deteriorated, clogging of the filter or the spinning nozzle occurs, or that the operating efficiency is deteriorated due to filaments breakage, so that the above mentioned effects are sufficiently attained.

Moreover, in the filament non-woven fabric of the present invention, by the preferred embodiment wherein the inorganic powder is at least one inorganic powder selected from the group consisting of titanium dioxide, silica, alum, calcium carbonate, calcium oxide, magnesium oxide and talc, preferably, the non-woven fabric can be obtained in which these inorganic powders have a relatively low nucleating efficiency, so that there is hardly any increase in the crystallization temperature of olefin copolymer, and the increase in the crystallization degree is remarkably small. Therefore, the properties of the low melting point component or low softening point olefin copolymer of the first component are not easily damaged and the hand feeling such as softness or touch etc. is good and the adhesive property to the other members is excellent.

Moreover, in the filament non-woven fabric of the present invention, by the preferred embodiment wherein the crystalline thermoplastic resin as the second component is polypropylene, preferably, the relatively soft filament non-woven fabric can be obtained.

Moreover, in the filament non-woven fabric of the present invention, by the preferred embodiment wherein the crystalline thermoplastic resin as the second component is polyethylene terephthalate, preferably, the filament non-woven fabric having the higher strength and more desirable elasticity (cushion property) at the time crimps are formed can be obtained.

Moreover, in the filament non-woven fabric of the present invention, by the preferred embodiment wherein the filament non-woven fabric is obtained by the spun bond method, the non-woven fabric having an excellent mechanical strength such as tensile strength easily can be obtained, and the productivity of the filament non-woven fabrics is very high because in this method, filaments obtained by melt spinning are opened and accumulated as it is. At the same time, the above mentioned effects are particularly effectively exhibited by the spun bond method and the conventional defects of the non-woven fabric comprising conjugated filaments obtained by the spun bond method can be improved.

Moreover, the absorbent article of the present invention can solve the problems of the conventional absorbent articles and can provide the absorbent articles in which the hand feeling such as softness or touch etc. is excellent and the adhesion to the other members is good. There are no problems in use, for example, layers constituting the absorbent article being peeled apart or the layer structure being not broken by using the above mentioned filament non-woven fabric for at least one portion of the absorbent article.

What is claimed is:

1. A filament non-woven fabric comprising thermoplastic conjugated filaments comprising at least one low melting point resin or low softening point resin that is selected from the group consisting of olefin binary copolymer and olefin terpolymer as a first component and crystalline thermoplastic resin as a second component; said thermoplastic filament containing inorganic powder in at least said first component, wherein the content of the inorganic powder is 500 to 50000 weight ppm with respect to the filament; wherein said non-woven fabric has a Uniformity Index of 80 or less.

2. The filament non-woven fabric according to claim 1, wherein the olefin terpolymer is ethylene-butene-propylene copolymer comprising 84 to 97 wt. % of propylene, 1 to 15 wt. % of 1-butene and 1 to 10 wt. % of ethylene.

3. The filament non-woven fabric according to claim 1, wherein the olefin binary copolymer is ethylene-propylene copolymer comprising 85 to 99 wt. % of propylene and 1 to 15 wt. % of ethylene.

4. The filament non-woven fabric according to claim 1, wherein the olefin binary copolymer is butene-propylene copolymer comprising 50 to 99 wt. % of propylene and 1 to 50 wt. % of 1-butene.

5. The filament non-woven fabric according to claim 1, wherein the olefin binary copolymer is ethylene-octene copolymer comprising 73 to 99 wt. % of ethylene and 1 to 27 wt. % of 1-octene.

6. The filament non-woven fabric according to claim 1, wherein the average particle diameter of the inorganic powder is in the range of 0.04 to 2 $\mu$m.

7. The filament non-woven fabric according to claim 1, wherein the inorganic powder is at least one inorganic powder selected from the group consisting of titanium dioxide, silica, alum, calcium carbonate, calcium oxide, magnesium oxide and talc.

8. The filament non-woven fabric according to claim 1, wherein the crystalline thermoplastic resin as the second component is polypropylene.

9. The filament non-woven fabric according to claim 1, wherein the crystalline thermoplastic resin as the second component is polyethylene terephthalate.

10. The filament non-woven fabric according to claim 1, which is obtained by the spun bond method.

11. An absorbent article using the filament non-woven fabric according to any of claim 1 for at least one portion of the absorbent article.

* * * * *